US009220572B2

United States Patent
Meridew et al.

(10) Patent No.: US 9,220,572 B2
(45) Date of Patent: Dec. 29, 2015

(54) METHOD FOR IMPLANTING A HIP PROSTHESIS AND RELATED SYSTEM

(71) Applicant: Biomet Manufacturing, LLC, Warsaw, IN (US)

(72) Inventors: Jason Meridew, Warsaw, IN (US); William Jason Slone, Silver Lake, IN (US); Mark Scrafton, Warsaw, IN (US); John White, Winona Lake, IN (US); Seth Nash, Columbia City, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/069,687

(22) Filed: Nov. 1, 2013

(65) Prior Publication Data

US 2014/0277555 A1    Sep. 18, 2014

Related U.S. Application Data

(60) Provisional application No. 61/783,230, filed on Mar. 14, 2013.

(51) Int. Cl.
*A61F 2/32* (2006.01)
*A61B 19/00* (2006.01)

(52) U.S. Cl.
CPC ....... *A61B 19/5225* (2013.01); *A61B 2019/262* (2013.01); *A61B 2019/505* (2013.01); *A61B 2019/5229* (2013.01)

(58) Field of Classification Search
CPC ................... A61B 2019/262; A61B 19/5225; A61F 2/4607
See application file for complete search history.

(56) References Cited

U.S. PATENT DOCUMENTS

| | | | |
|---|---|---|---|
| 6,205,411 B1 * | 3/2001 | DiGioia et al. | 703/11 |
| 6,988,009 B2 | 1/2006 | Grimm et al. | |
| 7,780,681 B2 | 8/2010 | Sarin et al. | |
| 8,167,823 B2 | 5/2012 | Nycz et al. | |
| 8,579,985 B2 | 11/2013 | Podolsky et al. | |
| 2004/0153191 A1 | 8/2004 | Grimm et al. | |
| 2007/0015999 A1 * | 1/2007 | Heldreth et al. | 600/408 |
| 2010/0261998 A1 | 10/2010 | Stiehl | |

OTHER PUBLICATIONS

Callanan, Mark C., et al. "Quality Improvement Through a Joint Registry at a Tertiary Hospital", The John Charnley Award, Risk Factors for Cup Malpositioning. Symposium: Papers Presented at the Hip Society Meeting 2010, The Association of Bone and Joint Surgeons, 2010.

* cited by examiner

*Primary Examiner* — Brian Dukert
(74) *Attorney, Agent, or Firm* — Schwegman Lundberg & Woessner, P.A.

(57) ABSTRACT

A method of implanting a hip joint prosthesis into a patient can include obtaining image data of hip joint anatomy of the patient. Physical activities that the patient desires to participate in subsequent to implanting the hip prosthesis can be determined. A size and an initial placement of the hip joint prosthesis based on the image data can be determined. A desired range of motion of the hip joint prosthesis based on the determined physical activities can be determined. A plan can be created comprising a desired implanted location of the hip joint prosthesis and based on the desired range of motion. The plan can be incorporated onto a guide. The plan can be executed with the guide thereby implanting the hip joint prosthesis into the patient at the desired implanted position.

12 Claims, 6 Drawing Sheets

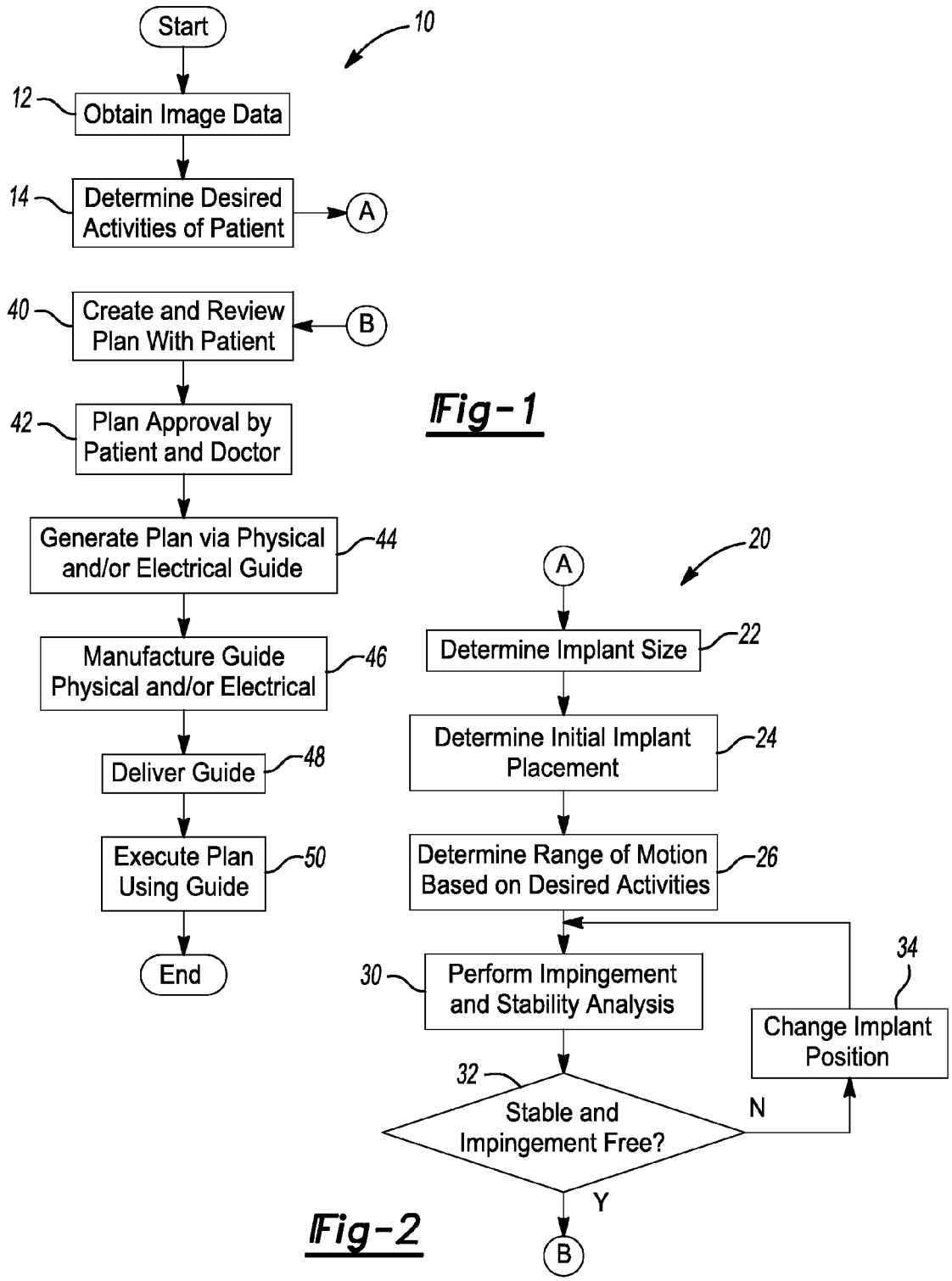

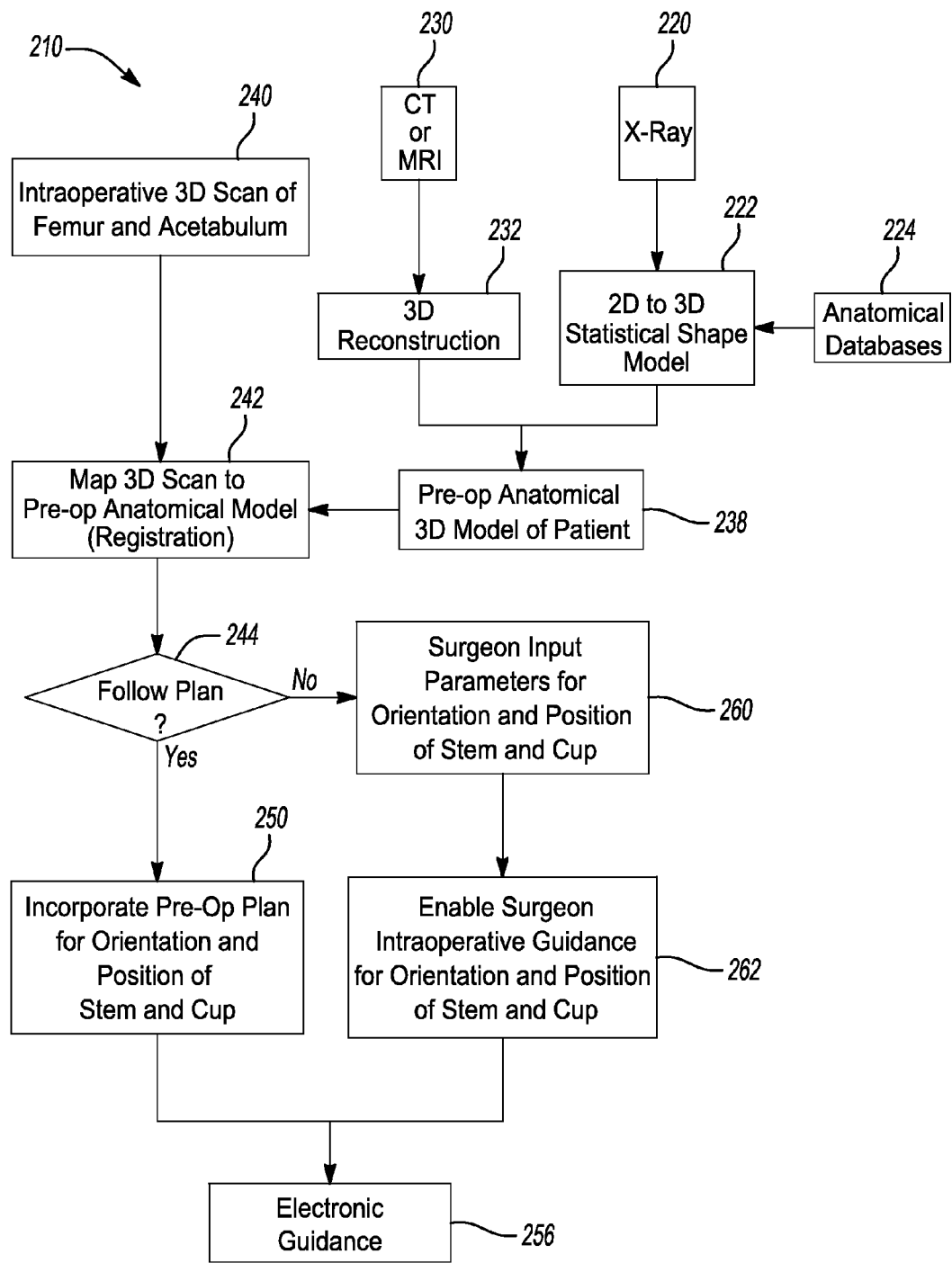

METHOD FOR IMPLANTING A HIP PROSTHESIS AND RELATED SYSTEM

CROSS-REFERENCE TO RELATED APPLICATIONS

This application claims the benefit of U.S. Provisional Application No. 61/783,230 filed on Mar. 14, 2013. The disclosure of the above application is incorporated herein by reference.

FIELD

The present disclosure relates to hip arthroplasty and more particularly relates to a method for performing hip arthroplasty.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Prosthetic joints can reduce pain due to arthritis, deterioration, deformation, and the like. Prosthetic hip joints often include a femoral component that is fixed to the patient's femur and an acetabular cup that is fixed within the patient's pelvis. More specifically, the femoral component can include a distal stem that extends into the patient's resected femur and a proximal body having a rounded head that is received within the acetabular cup. The head can articulate within the cup so as to moveably couple the femoral component within the acetabular cup. While traditional hip arthroplasty has achieved relative success in terms of results and patient satisfaction, a need exists to provide additional refinement of acetabular cup placement and implant orientation to facilitate more active lifestyles.

SUMMARY

A method of implanting a hip joint prosthesis into a patient can include obtaining image data of hip joint anatomy of the patient. Physical activities that the patient desires to participate in subsequent to implanting the hip prosthesis can be determined. A size and an initial placement of the hip joint prosthesis based on the image data can be determined. A desired range of motion of the hip joint prosthesis based on the determined physical activities can be determined. A plan can be created comprising a desired implanted location of the hip joint prosthesis and based on the desired range of motion. The plan can be incorporated onto one of a tool and a guide. The plan can be executed with the tool or guide thereby implanting the hip joint prosthesis into the patient at the desired implanted location.

According to additional features, executing the plan with the tool or guide can further comprise providing feedback to a surgeon with the tool or guide. The feedback can be based on an actual position of the hip joint prosthesis relative to the desired implanted location of the hip joint prosthesis. A desired orientation of the hip joint prosthesis can be determined. The desired orientation can include a target inclination angle and a target anteversion angle. The desired orientation can be incorporated into the plan.

In additional features, the hip joint anatomy of the patient is registered with the plan. Registering can include performing a three-dimensional scan of the hip joint anatomy. Anatomical surfaces of the femur and acetabulum of the hip joint anatomy can be mapped.

The plan can be incorporated onto eyewear worn by a surgeon. The plan can be executed by projecting data related to the plan onto the eyewear worn by the surgeon. In other configurations, the plan can be incorporated onto an electronic display associated with a hip insertion instrument. The plan can be displayed onto the electronic display. In still other configurations, the plan can be incorporated onto an acetabular cup insertion instrument.

In some examples, at least one of tactile and audible feedback can be provided based on an actual position of an acetabular cup of the hip joint prosthesis relative to the desired implanted location of the hip joint prosthesis. An impingement and stability analysis can be performed. The desired implanted position can be modified based on detecting of at least one of impingement and instability of the hip joint prosthesis. The plan can be created based on at least one of the hip joint anatomy of the patient and a database of pelves having anatomical characteristics substantially similar to the patient. In one example, obtaining image data can include (i) creating a virtual anatomical three-dimensional model of the patient's hip joint, (ii) obtaining an actual partial scan of the patient's hip joint; and (iii) registering the partial scan to the virtual anatomical three-dimensional model.

According to additional examples, a method of implanting a hip joint prosthesis into a patient can include obtaining image data of hip joint anatomy of the patient. Physical activities that the patient desires to participate in subsequent to implanting the hip prosthesis can be determined. A size and an initial placement of the hip joint prosthesis based on the image data can be determined. A desired range of motion of the hip joint prosthesis based on the determined physical activities can be determined. A plan can be created comprising a desired implanted location of the hip joint prosthesis and based on the desired range of motion. The plan can be incorporated onto a visual guide. An implantation template can be displayed onto the visual guide. The implantation template can have information from the plan related to the desired location and position of the hip joint prosthesis. The implantation template can be referenced while implanting the hip joint prosthesis into the patient at the desired implanted position.

Displaying the implantation template can comprise displaying at least one of a target inclination angle and a target anteversion angle. An indication of implantation depth of a femoral component and/or an acetabular cup can be displayed. A vector of a femoral component position and/or an acetabular cup insertion angle can be displayed.

According to additional examples, a method of implanting a hip joint prosthesis into a patient can include obtaining image data of hip joint anatomy of the patient. Physical activities that the patient desires to participate in subsequent to implanting the hip prosthesis can be determined. A size and an initial placement of the hip joint prosthesis based on the image data can be determined. A desired range of motion of the hip joint prosthesis based on the determined physical activities can be determined. A plan can be created comprising a desired implanted location of the hip joint prosthesis and based on the desired range of motion. The plan can be incorporated onto an electrical guide. The desired implanted location and position can be provided with the electrical guide.

The electrical guide can be referenced while implanting the hip joint prosthesis into the patient at the desired implanted position.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 1 is a flowchart of a method of implanting a hip prosthesis into a patient according to one example of the present disclosure;

FIG. 2 is a flowchart of an analysis portion of the method shown in FIG. 1;

FIG. 9 is a flowchart of an optical scanning method according to one example of the present disclosure Corresponding reference numerals indicate corresponding parts throughout the several views of the drawings.

DETAILED DESCRIPTION

Figure 3:
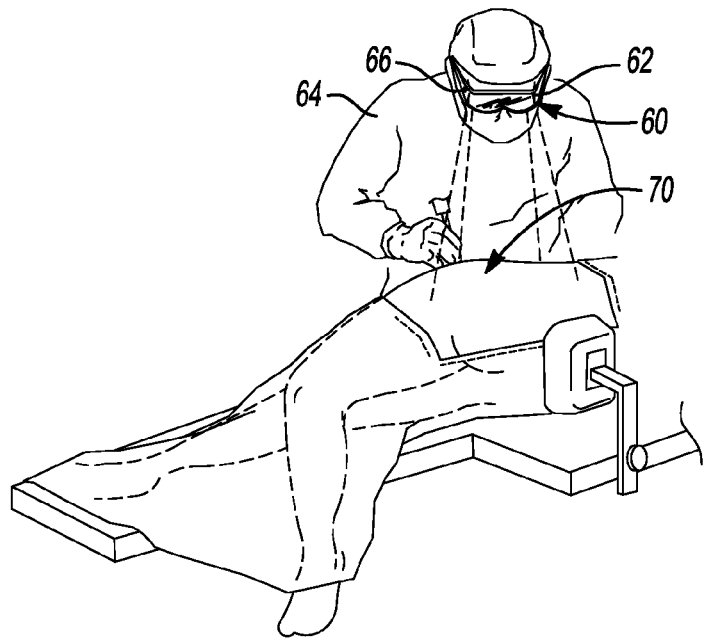
FIG. 3 is a perspective view of a surgeon performing hip arthroplasty on a patient according to one example of the present disclosure.

For the purpose of enhancing the understanding of the principles of the present disclosure, reference will now be made to the examples illustrated in the drawings. While specific language will be used to describe the drawings, no limitation of the scope of the present disclosure is intended. The following description will be specifically directed toward a method of implanting a hip joint prosthesis. It will be appreciated however, that the present method may be equally applicable to methods for implanting other prosthesis including those associated with other joints including, but not limited to, a knee, a shoulder, an elbow and an ankle.

With initial reference to FIG. 1, a method of implanting a hip joint prosthesis into a patient is shown and generally identified at reference numeral 10. In general, the method 10 illustrates one example of a work flow established between a patient and an orthopedic surgeon to select an optimal hip joint prosthesis for the particular patient. More particularly, the method 10 allows a surgeon and patient to select an optimal hip joint prosthesis that will permit the patient to participate in various physical activities identified by the patient. In this regard, some patients may desire a hip joint prosthesis more suitable for an active lifestyle while other patients may require a hip joint prosthesis particularly suited for less active lifestyles. As will be discussed herein, various target implant positions and locations may be particularly suited for patients wanting to participate in certain physical activities subsequent to implantation. The method 10 therefore can provide a custom or patient-specific hip joint prosthesis to the patient.

At block 12, image data of the hip joint anatomy of the patient is obtained. The image data can be any suitable image data such as, but not limited to, an X-ray, a CT scan, an MRI, an ultrasound, a fluoroscopic scan or a collection of motion data. It will be appreciated that the image data may be two-dimensional or three-dimensional. In block 14 the desired activities of the patient are determined. According to one example, the patient can identify physical activities that they desire to participate. Physical activities can include activities of daily living. In this regard, some patients may desire a hip joint prosthesis that can provide the patient with a range of motion suitable for participating in such physical activities. It will be appreciated that the physical activities can include any physical activity such as, by way of example, yoga, downhill skiing, kick-boxing, rowing, etc.

Once the desired activities of the patient are determined, the method performs an analysis generally identified at reference 20 in FIG. 2. In block 22 an implant size is determined. In one example, the implant size can be determined at least in part by the image data. In general, implant size can comprise a size for all components of the hip joint prosthesis such as a femoral component, an acetabular component, a modular head and a liner. In block 24 an initial implant placement is determined. In block 26 a desired range of motion of the hip joint prosthesis is determined based on the determined physical activities. Those skilled in the art will readily appreciate that certain physical activities will require a range of motion that may be different than another physical activity. In step 30 an impingement and stability analysis is performed. In one example, the impingement and stability analysis can be performed virtually.

In block 32 it is determined whether the hip joint prosthesis is stable and impingement free. If the hip joint prosthesis is not stable and impingement free, the position of the hip joint prosthesis is changed in step 34. If the hip joint prosthesis is stable and impingement free, a plan is created and reviewed with the patient in block 40 (FIG. 1). As used herein, the term "plan" is used to denote a preoperative plan having data relating to a target position and orientation of an implanted hip joint prosthesis. As will become appreciated, the plan can be a data file that can be stored on a physical data storage medium and/or communicated wirelessly between components in an operating room including, but not limited to, a workstation, a tablet, a mobile phone, a surgical instrument, an implant, a wearable accessory or garment, etc.

The plan can include a desired implanted location of the hip joint prosthesis based on the desired range of motion. The plan can additionally or alternatively include a desired orientation of the hip joint prosthesis including a target inclination angle and a target anteversion angle. The plan may also include an indication of a desired implantation depth of components of the hip joint prosthesis including a femoral component and an acetabular cup. In additional configurations, the plan may also incorporate vector orientations of components of the hip joint prosthesis including the femoral component and the acetabular cup. Furthermore, the plan can be created based on the hip joint anatomy of the patient and/or a database of pelves having anatomical characteristics substantially similar to the patient.

In block 42, the plan is approved by the patient and the doctor. In block 44, the plan is generated by way of a mechanical (physical) guide and/or an electrical guide. Various examples of such guides will be described herein. In step 46, the guide is manufactured. In step 48 the guide is delivered to the surgeon. In step 50 the plan is executed using the guide. Various examples will be provided herein for executing the plan using the guide.

With reference now to FIG. 3, an exemplary guide 60 according to the present disclosure is shown. The guide 60 is in the form of a visual guide and comprises eyewear 62 that may be worn by a surgeon 64. The guide 60 can include a two or three-dimensional visual image or lighted guidance projected or otherwise viewable with the eyewear 62. The visual image can include an implantation template (as will be described herein with respect to FIGS. 5 and 7A-7C) that includes the desired implanted location and orientation of a selected hip joint prosthesis 70. According to one configuration, the plan can be downloaded electronically onto a memory chip 66 that is incorporated onto the guide 60. Those skilled in the art will appreciate that the plan can additionally or alternatively be communicated to the guide 60 wirelessly. In other examples, the plan could reside on a radio frequency identification (RFID) device that is attached or worn by the patient.

Figure 4:
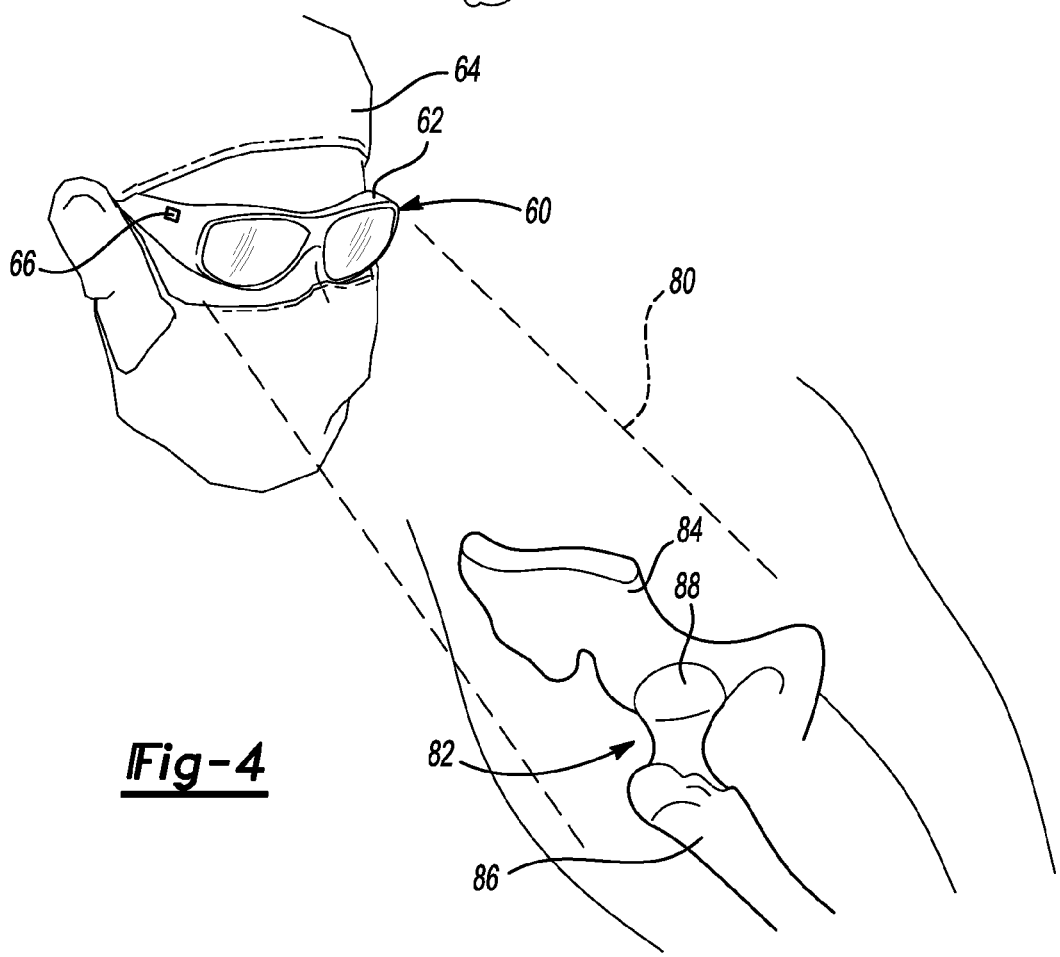
FIG. 4 is a perspective view of a view path the surgeon visualizes with a guide loaded with a preoperative plan developed from the method of FIG. 1.

With reference to FIG. 4, a viewing path 80 provided with the visual guide 60 can further enable the surgeon 64 to view a hologram of a hip joint 82 including an acetabulum 84 and femur 86 including a femoral head 88. The hologram may enable the surgeon to view skeletal anatomy of the hip joint 82 while the skeletal anatomy is otherwise blocked from view by soft tissue.

Figure 5:
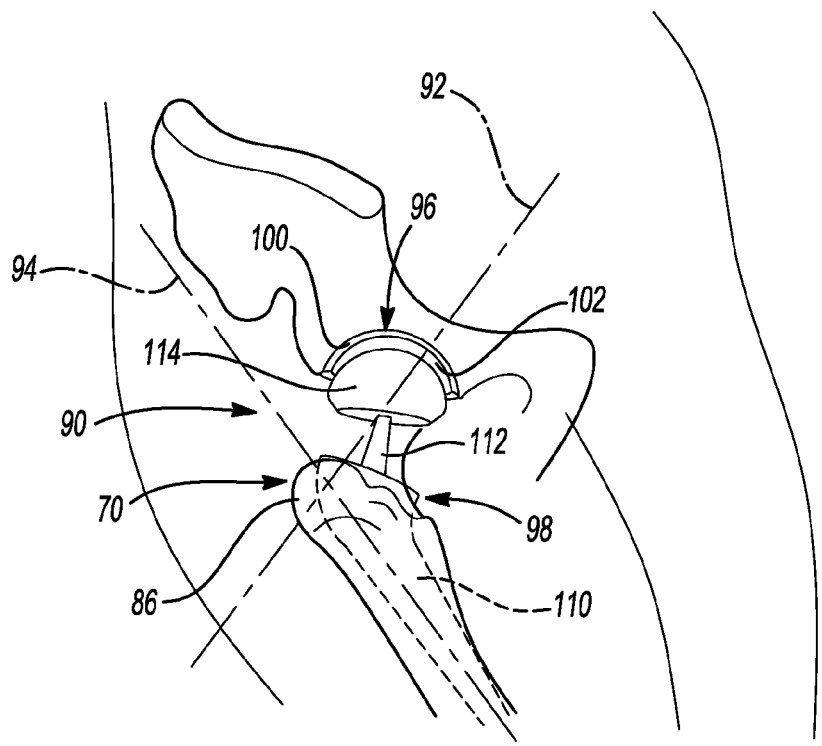
FIG. 5 is a first exemplary implantation template created by the preoperative plan and viewed from a guide according to the present disclosure.

Turning now to FIG. 5, the guide 60 can also be configured to display location information of the hip prosthesis 70 according to the plan including a first implantation template 90. Briefly, the hip prosthesis 70 can generally include an acetabular cup assembly 96 and a femoral component 98. The acetabular cup assembly 96 can have an acetabular cup 100 and a liner 102. The femoral component 98 can include a femoral stem 110, an adapter 112 and a femoral ball 114. The first implantation template 90 can include a first vector 92 indicative of a desired position of the acetabular cup 100 and a second vector 94 indicative of a desired position of the femoral stem 110.

Figure 6:
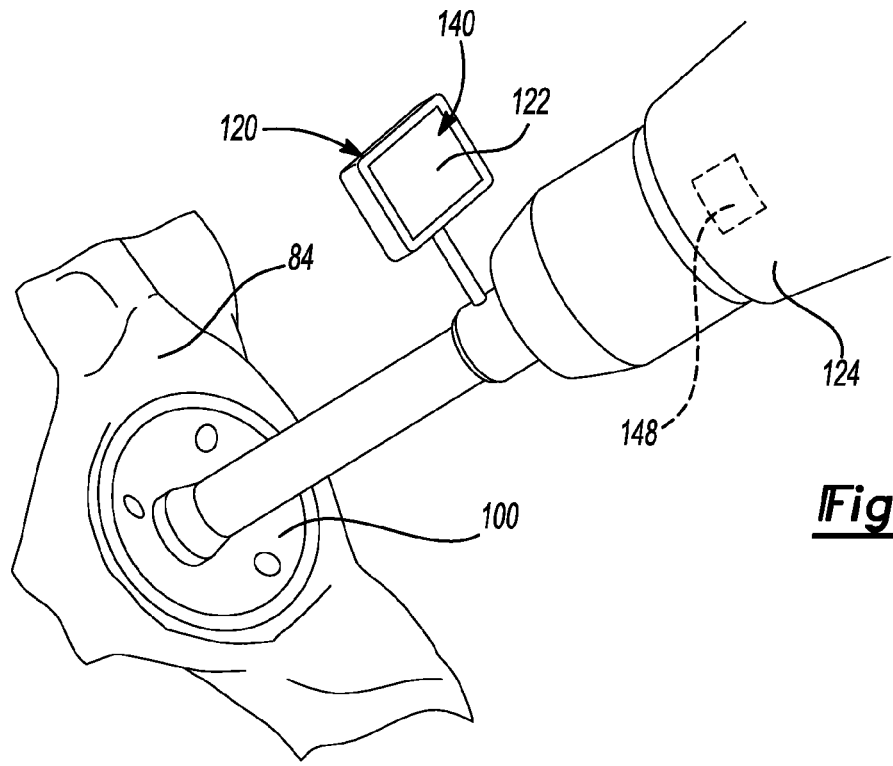
FIG. 6 is a perspective view of another guide constructed in accordance to another example of the present disclosure.
Figure 7C:
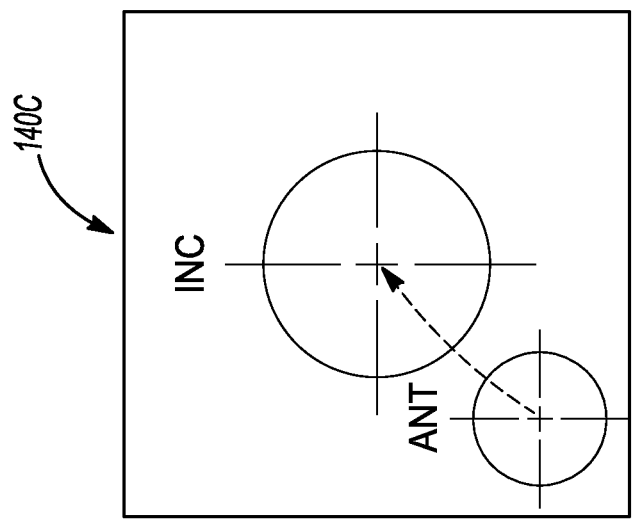
FIGS. 7A-7C are additional exemplary implantation templates created by the preoperative plan and viewed from a guide according to the present disclosure.

With reference now to FIG. 6, another exemplary guide 120 according to the present disclosure is shown. The guide 120 is in the form of a visual guide and comprises an electronic display 122 incorporated onto a hip insertion instrument 124. The guide 120 can provide a visual image or lighted guidance projected or otherwise viewable on the electronic display 122. The electronic display 122 can display one or more implantation templates collectively identified at reference 140 in FIG. 6 and individually identified at references 140A (FIG. 7A), 140B (FIG. 7B) and 140C (FIG. 7C). Additionally or alternatively, the electronic display 122 can display the first implantation template 90 (FIG. 5). The implantation templates 140 include the desired implanted location of a selected hip joint prosthesis 70.

According to one configuration, the plan can be downloaded electronically onto a memory chip 148 that is incorporated onto the hip insertion instrument 124. Those skilled in the art will appreciate that the plan can additionally or alternatively be communicated to the guide 120 wirelessly. In other examples, the plan could reside on a radio frequency identification (RFID) device that is attached or worn by the patient.

Figure 7B:
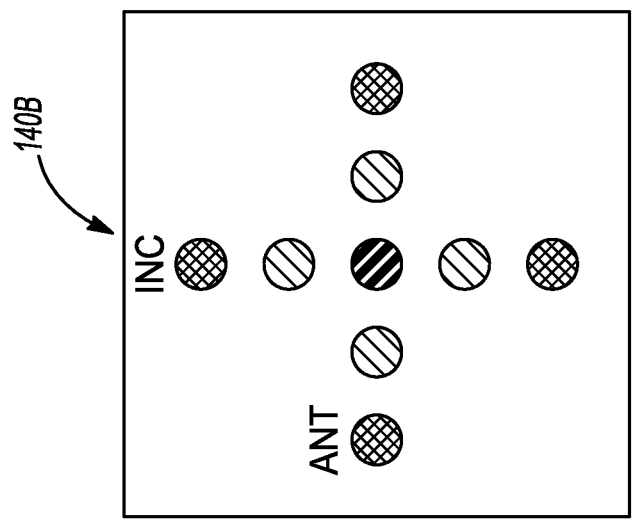
Figure 7A:
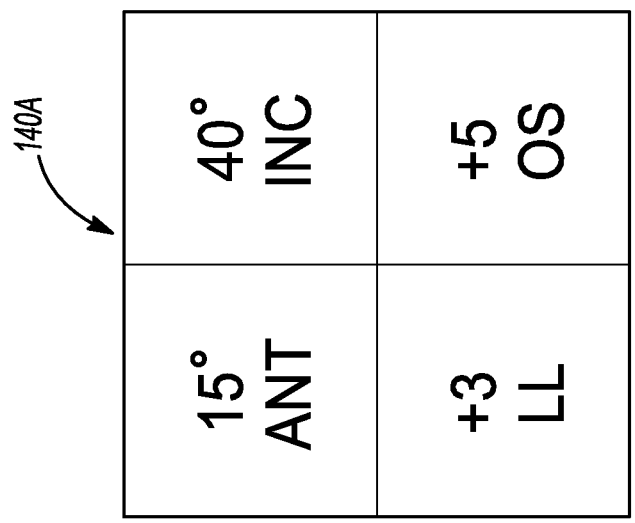

With reference now to FIGS. 7A, 7B and 7C, the exemplary implantation templates 140A, 140B and 140C will be described. The implantation template 140A can include graphics corresponding to the target anteversion angle (ANT), target inclination angle (INC), leg length (LL) and offset (OS) according to the plan. In this regard, a surgeon can view this information intraoperatively such as on the guide 60 (FIG. 3) or the guide 120 (FIG. 6). The implantation template 140B can include visual indicators such as lights that illuminate as the cup 100 (or other component of the hip prosthesis 70) approaches a corresponding position of the plan. The implantation template 140C can display an actual position of the cup 100 and the desired position of the cup 100. In some implementations, some or all of the implantation templates 90, 140A, 140B and 140C can be displayed concurrently or superimposed on the guide 60 or 120. It will be appreciated that any of the implantation templates 90 or 140 disclosed herein may additionally or alternatively be displayed elsewhere, such as on a workstation, a mobile phone, a tablet or other device.

Figure 8:
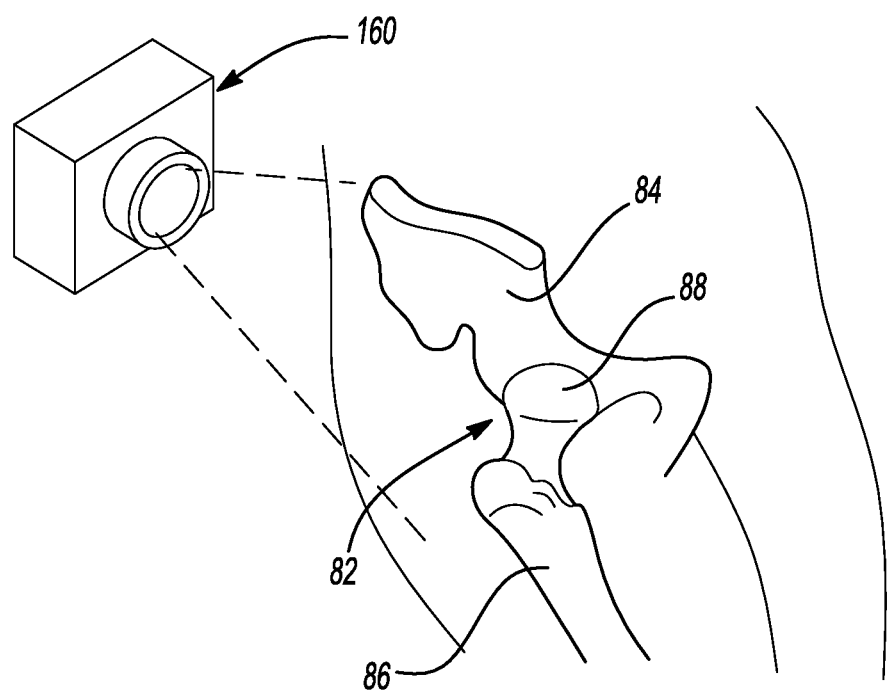
FIG. 8 is a perspective view of a three-dimensional scanner used to map anatomical surfaces of a patient's anatomy.

Turning now to FIG. 8, a three-dimensional imaging device or scanner 160 may be used to map anatomical surfaces of the femur 86 and acetabulum 84. According to one example, various points around the acetabulum 84 may be touched (such as with a probe) and stored to register the anatomy of the patient to the plan. Other areas of the patient's anatomy, such as the femur 86 may additionally or alternatively be registered to correlate with the plan. With the anatomical surfaces of the femur 86 and acetabulum 84 registered, the location of the anatomy is known. This information can be used with any of the guides disclosed herein. It will be further appreciated that the guides disclosed herein are not mutually exclusive. In this regard, in some examples a surgeon may use multiple guides while implanting the hip joint prosthesis 70.

With reference now to FIG. 9, an optical scanning method or method of obtaining image data according to one example of the present disclosure is shown and generally identified at reference numeral 210. As used herein, the term "joint space" is used to generally refer to anatomical landmarks related to a hip including but not limited to a pelvis, an acetabulum, and a femoral head. In one option, a pre-operative or virtual patient-specific anatomical three-dimensional (3D) model of a patient can be created at block 238. In one example, an x-ray or other two-dimensional (2D) images can be obtained at block 220. In block 222, the 2D images obtained at block 220 can be converted to a 3D statistical shape model. Additionally or alternatively, the 3D statistical shape model can be created by referencing data from known anatomical databases in block 224. For example, the anatomical databases 224 can have data representing joint spaces from many known patients. This data can be used as a reference to merge with the 2D image data of the patient obtained at block 220 to create a complete virtual 3D statistical shape of the patient's joint space. In one advantage, the cost associated with obtaining actual 3D images of the patient can be mitigated by requiring only traditional x-ray images and leveraging known data of the anatomical databases to create a 3D model.

In another example, a CT and/or MRI can be obtained in block 230. From the CT and/or MRI data, a 3D reconstruction of the joint space can be created in block 232. In this regard, the virtual anatomical 3D model of a complete joint space can be created at block 238 from either using traditional 2D x-ray data (block 220), or using CT/MRI data (block 230).

In block 240, an intraoperative 3D scan of a patient's joint space is obtained. In one example, an incision can be made on the patient and image data can be obtained such as by laser imaging, white light imaging, blue light imaging, optical imaging and ultrasound imaging. It will be appreciated that in some instances, positional information of a patient's entire joint space may be incomplete from block 240. In this regard, in many instances, the intraoperative 3D scan obtained in block 240 may only represent a small (incomplete) window of data of the patient's joint space. In block 242, a complete 3D model is created by mapping the (incomplete) 3D scan of the patient's actual joint space taken at block 240 with the (complete) virtual anatomical 3D model created in block 238. Explained further, the surface data obtained from the intraoperative 3D scan from block 240 can be registered to the virtual anatomical 3D model from block 238.

In one method, the surface data obtained from the intraoperative 3D scan can be superimposed or layered onto the surface data obtained from the virtual anatomical 3D model and a best fit analysis of the two surfaces together can be obtained. In this regard, an efficient method of registering the small window of a patient's actual anatomy to a virtual anatomical 3D model can be provided. A complete anatomical 3D model can be created from otherwise incomplete data obtained from an intraoperative 3D scan. Anatomical landmarks and surface features of the patient's joint space can be registered to a pre-operative image allowing a smart instrument, smart implant or computer navigation equipment to identify a position and orientation of a patient's anatomy without the need for physical probes, measurements or other manual means of identifying points.

In block 244 a surgeon can determine whether the preoperative plan (discussed above) will be followed or if a surgeon prefers to position implants based on a personal plan or personal preferences. Explained further, in some examples, a surgeon may decide to follow the preoperative plan or, alternatively, may decide once the joint space is opened up, to position an implant in another location/orientation based upon the surgeon's personal real time analysis of the patient's joint space. If the surgeon decides to follow the preoperative plan, the preoperative plan for position and orientation of the stem and cup is incorporated in block 250.

Alternatively, if the surgeon determines to follow personal preference, the surgeon can input parameters for position and orientation of the stem and cup in block 260. When using a surgeon's personal analysis, the surgeon may decide upon a desired position (including inclination and anteversion for example) of an acetabular cup. The surgeon can then proceed with intraoperative guidance for position and orientation of the stem and cup in block 262.

In block 256 electronic guidance can be provided. The desired position (either from the preoperative plan, or from the surgeon's preference) can be input onto a smart instrument that can convey to the surgeon when the desired orientation and position of the acetabular cup and stem has been attained. In one example, an acetabular inserter may have a guide that can display actual and desired positions of the acetabular cup (see FIGS. 6-7C above) to further assist the surgeon in locating the acetabular cup at the desired position and orientation. Such an inserter could convey to the surgeon when the desired position and orientation of the acetabular cup has been reached. According to another example, a mold can be taken of the joint space such as with putty, molding clay or other medium. The mold can then be optically scanned into a 3D image. A landmark can be optionally placed in the joint space and be molded with the anatomy. Optical scanners can be used to collect data from the mold and register or relate the data to a pre-operative image using image recognition software.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting a hip joint prosthesis into a patient, the method comprising:
    obtaining image data of hip joint anatomy of the patient;
    determining physical activities the patient desires to participate in subsequent to implanting the hip joint prosthesis;
    determining a size and an initial placement of the hip joint prosthesis based on the image data;
    determining a desired range of motion of the hip joint prosthesis based on the determined physical activities;
    creating a plan comprising a desired implanted location of the hip joint prosthesis and based on the desired range of motion;
    incorporating the plan onto a guide, the guide including eyewear worn by a surgeon;
    projecting a hologram of the hip joint anatomy of the patient onto the eyewear to be viewable by the surgeon;
    displaying an implantation template onto the eyewear, the implantation template including (i) a first vector indicative of the desired implanted location of an acetabular cup of the hip joint prosthesis, and (ii) a second vector indicative of the desired implanted location of a femoral stem of the hip joint prosthesis; and
    executing the plan with the guide thereby implanting the hip joint prosthesis into the patient at the desired implanted location.

2. The method of claim 1 wherein executing the plan further comprises:
    providing feedback to a surgeon with the guide based on an actual position of the hip joint prosthesis relative to the desired implanted location of the hip joint prosthesis.

3. The method of claim 1 wherein creating the plan further comprises:
    determining a desired orientation of the hip joint prosthesis including a target inclination angle and target anteversion angle; and
    incorporating the desired orientation into the plan.

4. The method of claim 1, further comprising registering the hip joint anatomy of the patient with the plan.

5. The method of claim 4 wherein registering the hip joint anatomy comprises:
    performing a three-dimensional scan of the hip joint anatomy; and
    mapping anatomical surfaces of a femur and acetabulum of the hip joint anatomy.

6. The method of claim 1, further comprising:
    performing an impingement and stability analysis; and
    modifying the desired implanted position based on detecting of at least one of impingement and instability of the hip joint prosthesis.

7. The method of claim 1 wherein creating the plan further comprises:
    creating the plan based on at least one of the hip joint anatomy of the patient and a database of pelves having anatomical characteristics substantially similar to the patient.

8. The method of claim 1 wherein obtaining image data comprises:
    creating a virtual anatomical three-dimensional model of the patient's hip joint;

obtaining an actual partial scan of the patient's hip joint; and registering the partial scan to the virtual anatomical three-dimensional model.

9. A method of implanting a hip joint prosthesis into a patient, the method comprising:

obtaining image data of hip joint anatomy of the patient;

determining physical activities the patient desires to participate in subsequent to implanting the hip joint prosthesis;

determining a size and an initial placement of the hip joint prosthesis based on the image data;

determining a desired range of motion of the hip joint prosthesis based on the determined physical activities;

creating a plan comprising a desired implanted location and position of the hip joint prosthesis based on the desired range of motion;

incorporating the plan onto a visual guide comprising eyewear worn by a surgeon;

projecting a hologram of the hip joint anatomy of the patient onto the eyewear to be viewable by the surgeon;

displaying an implantation template onto the visual guide, the implantation template having information from the plan related to the desired location and position of the hip joint prosthesis, the information including:

a target inclination angle;

a target anteversion angle;

an indication of implantation depth of at least one of a (i) femoral component, and (ii) acetabular cup; and a vector of at least one of a (i) femoral component position, and (ii) acetabular cup insertion angle and referencing the implantation template while implanting the hip joint prosthesis into the patient at the desired implanted position.

10. The method of claim 9 wherein executing the plan with the guide further comprises:

providing feedback to a surgeon with the guide based on an actual position of the hip joint prosthesis relative to the desired implanted location of the hip joint prosthesis.

11. The method of claim 9, further comprising:

performing an impingement and stability analysis; and modifying the desired implanted position based on detecting of at least one of impingement and instability of the hip joint prosthesis.

12. The method of claim 9 wherein creating the plan further comprises:

creating the plan based on at least one of the hip joint anatomy of the patient and a database of pelves having anatomical characteristics substantially similar to the patient.

* * * * *